United States Patent
Fujita et al.

(10) Patent No.: US 10,888,532 B2
(45) Date of Patent: Jan. 12, 2021

(54) BUTORPHANOL-CONTAINING PATCH

(71) Applicant: HISAMITSU PHARMACEUTICAL CO., INC., Tosu (JP)

(72) Inventors: Naoko Fujita, Tsukuba (JP); Takito Shima, Tsukuba (JP); Kazuya Kominami, Tsukuba (JP); Naoyuki Uchida, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 0 days.

(21) Appl. No.: 16/471,692

(22) PCT Filed: Dec. 21, 2017

(86) PCT No.: PCT/JP2017/045995
§ 371 (c)(1),
(2) Date: Jun. 20, 2019

(87) PCT Pub. No.: WO2018/123822
PCT Pub. Date: Jul. 5, 2018

(65) Prior Publication Data
US 2020/0000737 A1  Jan. 2, 2020

(30) Foreign Application Priority Data
Dec. 28, 2016 (JP) .................. 2016-255034

(51) Int. Cl.
| A61K 9/70 | (2006.01) |
| A61K 31/485 | (2006.01) |
| A61K 47/10 | (2017.01) |
| A61K 47/14 | (2017.01) |
| A61K 47/34 | (2017.01) |

(52) U.S. Cl.
CPC .......... *A61K 9/7053* (2013.01); *A61K 9/7069* (2013.01); *A61K 31/485* (2013.01); *A61K 47/10* (2013.01); *A61K 47/14* (2013.01); *A61K 47/34* (2013.01)

(58) Field of Classification Search
CPC .................................................. A61K 9/7053
See application file for complete search history.

(56) References Cited

U.S. PATENT DOCUMENTS

| 3,775,414 A | 11/1973 | Monkovic et al. |
| 2006/0078600 A1 | 4/2006 | Muller |
| 2009/0246265 A1* | 10/2009 | Stinchcomb ......... A61K 31/485 424/449 |
| 2014/0161865 A1 | 6/2014 | Higo et al. |
| 2015/0004215 A1 | 1/2015 | Yoshizaki et al. |
| 2017/0224630 A1 | 8/2017 | Noguchi et al. |

FOREIGN PATENT DOCUMENTS

| EP | 2 740 472 A1 | 6/2014 |
| EP | 2 818 161 A1 | 12/2014 |
| JP | 2004-536054 A | 12/2004 |
| JP | 2006-001859 A | 1/2006 |
| JP | 2006-045099 A | 2/2006 |
| WO | 02/089778 A2 | 11/2002 |
| WO | 2016/060122 A1 | 4/2016 |

OTHER PUBLICATIONS

Michal Svozil et al., "In Vitro Studies on Transdermal Permeation of Butorphanol", Drug Development and Industrial Pharmacy, pp. 559-567, 2007, vol. 33.
International Search Report for PCT/JP2017/045995, dated Mar. 13, 2018.
International Preliminary Report on Patentability and Written Opinion dated Jul. 11, 2019 in International Application No. PCT/JP2017/045995.
U.S. Appl. No. 16/604,311, Hisamitsu Pharmaceutical Co., Inc, filed Oct. 10, 2019.
U.S. Appl. No. 16/605,268, Hisamitsu Pharmaceutical Co., Inc, filed Oct. 15, 2019.
Extended European Search Report dated Apr. 22, 2020, from the European Patent Office in Application No. 17889363.2.
Communication dated Sep. 10, 2020 from Japanese Patent Office in JP Application No. 2018-559128.

* cited by examiner

*Primary Examiner* — Benjamin J Packard
(74) *Attorney, Agent, or Firm* — Sughrue Mion, PLLC

(57) ABSTRACT

A patch comprising:
a backing layer; and
an adhesive layer, wherein
the adhesive layer contains at least one drug selected from the group consisting of butorphanol and pharmaceutically acceptable salts thereof and a silicone-based adhesive base, and
a mass per unit area of the adhesive layer is 30 to 90 g/m².

9 Claims, No Drawings

BUTORPHANOL-CONTAINING PATCH

CROSS REFERENCE TO RELATED APPLICATIONS

This Application is a National Stage of International Application No. PCT/JP2017/045995 filed Dec. 21, 2017, claiming priority based on Japanese Patent Application No. 2016-255034 filed Dec. 28, 2016.

TECHNICAL FIELD

The present invention relates to a butorphanol-containing patch, and more particularly to a patch containing butorphanol and/or a pharmaceutically acceptable salt thereof.

BACKGROUND ART

Butorphanol is a generic name for 17-(cyclobutylmethyl)morphinan-3,14-diol having a molecular structure of morphinan skeleton. Butorphanol is a drug that is classified as an opioid-based analgesic and is generally used as an injection containing butorphanol tartrate which is its tartaric acid addition salt. As such butorphanol, N-cyclobutylmethyl-3,14-dihydroxymorphinan is disclosed in U.S. Pat. No. 3,775,414 (PTL 1), for example.

In addition, for example, M. Svozil et al., Drug Development and Industrial Pharmacy, 2007, 33 (5), p. 559-67 (NPL 1) describes use of butorphanol as a drug for transdermal absorption preparations. Moreover, International Publication No. 2016/060122 (PTL 2) describes a patch which includes a backing layer and an adhesive layer, in which the adhesive layer contains at least one selected from the group consisting of butorphanol and pharmaceutically acceptable salts thereof, higher aliphatic alcohols, and polyvinylpyrrolidones which are non-crosslinked and do not contain vinyl acetate as a constituent monomer.

Furthermore, in general, transdermal absorption preparations have advantages such as reduced number of administration and easy administration and make it possible to achieve sustained release which is difficult with injections and the like. However, it is required to develop the efficacy more quickly depending on the therapeutic purpose of the drug to be administered. For example, Japanese Unexamined Patent Application Publication No. 2006-45099 (PTL 3) describes, as a transdermal absorption preparation intended to increase the initial release rate, a transdermal absorption patch (cataplasm) in which an aqueous ointment containing a pharmaceutically active ingredient is coated on a support at 100 to 360 g/m². However, no disclosure has yet been made so far of a butorphanol-containing patch with sufficiently quick development of butorphanol efficacy. In addition, the cataplasm containing the aqueous base as described in PTL 3 has a problem that the skin permeability and utilization rate of the drug may not be stabilized due to volatilization or inflow of the aqueous component when applying the cataplasm onto the skin.

CITATION LIST

Patent Literature

[PTL 1] U.S. Pat. No. 3,775,414
[PTL 2] International Publication No. 2016/060122
[PTL 3] Japanese Unexamined Patent Application Publication No. 2006-45099

Non Patent Literature

[NPL 1] M. Svozil et al., Drug Development and Industrial Pharmacy, 2007, 33, p. 559-567

SUMMARY OF INVENTION

Technical Problem

The present invention has been made in view of the above problem, and an object thereof is to provide a butorphanol-containing patch which has sufficiently quick efficacy development, that is, a sufficiently short lag time and maximum skin permeation rate reach time (Tmax) and which is excellent in drug skin permeability as well as sufficiently high in utilization rate of the drug.

Solution to Problem

The present inventors have made earnest studies to achieve the above object and found as a result that it is possible to sufficiently shorten the lag time (delay time) and the maximum skin permeation rate reach time (Tmax), that is, significantly accelerate the efficacy development of butorphanol when, in a patch including a backing layer and an adhesive layer, the adhesive layer contains at least one drug selected from the group consisting of butorphanol and pharmaceutically acceptable salts thereof (hereinafter referred to as the "butorphanol and/or a pharmaceutically acceptable salt thereof" in some cases) and a silicone-based adhesive base, and further, a mass per unit area of the adhesive layer is set in a range of particularly 30 to 90 g/m².

Lag time is also usually expressed by the following formula: lag time=(skin thickness)$^2$/(6×drug diffusion coefficient in skin). For this reason, it has been presumed that the lag time remains unchanged regardless of the mass per unit area of the adhesive layer of the patch as long as the blended ingredients and their content ratios considered to affect the drug diffusion coefficient are the same. However, the present inventors have found that, surprisingly, the lag time is shortened for the patch of the above configuration which has a mass per unit area of the adhesive layer within a specific range.

Moreover, the present inventors have found that the patch of the above configuration can develop excellent drug skin permeability (skin permeation rate and skin permeation amount of the drug) even when the content (absolute amount) of the drug decreases as the mass per unit area of the adhesive layer decreases. Furthermore, the present inventors have found that, as compared with the case of using a rubber-based adhesive base being a non-aqueous adhesive base as in the case of the silicone-based adhesive base, all of the skin permeation rate, the skin permeation amount, and the utilization rate of the drug are further increased in the patch of the above configuration. Thus, the present invention has been completed.

Specifically, a patch of the present invention is a patch comprising: a backing layer; and an adhesive layer, wherein the adhesive layer contains at least one drug selected from the group consisting of butorphanol and pharmaceutically acceptable salts thereof and a silicone-based adhesive base, and a mass per unit area of the adhesive layer is 30 to 90 g/m².

In the patch of the present invention, the adhesive layer preferably further contains at least one absorption enhancer selected from the group consisting of aliphatic alcohols and fatty acid esters, and the absorption enhancer is more preferably at least one selected from the group consisting of isostearyl alcohol, oleyl alcohol, octyldodecanol, and propylene glycol monolaurate. Moreover, a content of the absorption enhancer in the adhesive layer is preferably 2:1 to 1:4 in a mass ratio of butorphanol and/or a pharmaceutically acceptable salt thereof (mass of butorphanol and/or the pharmaceutically acceptable salt thereof in terms of a tartaric acid addition salt of butorphanol:mass of the absorption enhancer), and preferably 1.5 to 25% by mass relative to a total mass of the adhesive layer.

Furthermore, in the patch of the present invention, a content of butorphanol and/or the pharmaceutically acceptable salt thereof in the adhesive layer is preferably 3 to 9% by mass relative to the total mass of the adhesive layer in terms of a tartaric acid addition salt of butorphanol.

Additionally, in the patch of the present invention, a content of the silicone-based adhesive base in the adhesive layer is preferably 50 to 97% by mass relative to the total mass of the adhesive layer.

What is more, the patch of the present invention preferably further contains an adsorbent, and a content of the adsorbent in the adhesive layer is preferably 3:1 to 1:4 in a mass ratio of butorphanol and/or the pharmaceutically acceptable salt thereof (mass of butorphanol and/or the pharmaceutically acceptable salt thereof in terms of a tartaric acid addition salt of butorphanol:mass of the adsorbent), and is preferably 1 to 20% by mass relative to the total mass of the adhesive layer.

Advantageous Effects of Invention

The present invention makes it possible to provide a butorphanol-containing patch which has a sufficiently short lag time and maximum skin permeation rate reach time (Tmax) and which is excellent in drug skin permeability as well as sufficiently high in utilization rate of the drug.

DESCRIPTION OF EMBODIMENTS

Hereinafter, the present invention is described in detail with reference to its preferable embodiments.

A patch of the present invention is a patch comprising: a backing layer and an adhesive layer, wherein the adhesive layer contains at least one drug selected from the group consisting of butorphanol and pharmaceutically acceptable salts thereof and a silicone-based adhesive base, and a mass per unit area of the adhesive layer is 30 to 90 g/m².

The patch of the present invention includes a backing layer and an adhesive layer. The backing layer is not particularly limited as long as it can support the adhesive layer to be described later, and a known one as the backing layer of a patch can be employed as appropriate. Examples of the material of the backing layer according to the present invention include polyolefins such as polyethylene and polypropylene; ethylene-vinyl acetate copolymers, vinyl acetate-vinyl chloride copolymers, polyvinyl chlorides, and the like; polyamides such as nylon; polyesters such as polyethylene terephthalate (PET), polybutylene terephthalate, and polyethylene naphthalate; cellulose derivatives; and synthetic resins such as polyurethane, and metals such as aluminum. Among these, polyesters and polyethylene terephthalate are preferable from the viewpoints of the non-adsorbability for the drug and the impermeability for the drug. Example forms of the backing layer include sheet-type products such as films, sheets, sheet-shaped porous bodies, and sheet-shaped foams; fabrics such as woven fabric, knitted fabric (knit), and nonwoven fabric; foil; and laminates of these. In addition, although the thickness of the backing layer is not particularly limited, it is preferably in a range of 5 to 1000 μm from the viewpoints of ease of manufacturing and ease of operation when applying the patch.

The patch of the present invention may further include a release liner on a surface of the adhesive layer opposite to the backing layer. Examples of the release liner include films and sheets made of polyolefins such as polyethylene and polypropylene; ethylene-vinyl acetate copolymers, vinyl acetate-vinyl chloride copolymers, polyvinyl chlorides, and the like; polyamides such as nylon; polyesters such as polyethylene terephthalate; cellulose derivatives; and synthetic resins such as polyurethane, and aluminum and paper, and laminates thereof. These release liners are preferably ones which have been subjected to release treatment such as coating with a fluorine-containing compound on the surface in contact with the adhesive layer for the purpose of facilitating peeling from the adhesive layer.

The adhesive layer according to the present invention contains as the drug at least one selected from the group consisting of butorphanol and pharmaceutically acceptable salts thereof. In the present invention, butorphanol indicates 17-(cyclobutylmethyl)morphinan-3,14-diol represented by the molecular formula $C_{21}H_{29}NO_2$.

In the present invention, the form of butorphanol contained in the adhesive layer may be a free form or a pharmaceutically acceptable salt thereof, a free form obtained by desalting of a pharmaceutically acceptable salt of butorphanol in a preparation during manufacturing and/or already manufactured, or one of these or a mixture of two or more of these. The pharmaceutically acceptable salt of butorphanol is preferably an acid addition salt from the viewpoint that this tends to improve the stability of the drug, and examples of the acid addition salt include hydrochloric acid, sulfuric acid, nitric acid, phosphoric acid, phosphorous acid, hydrobromic acid, maleic acid, malic acid, ascorbic acid, tartaric acid, lauric acid, stearic acid, palmitic acid, oleic acid, myristic acid, lauryl sulfuric acid, linolenic acid, and fumaric acid. Among these, the pharmaceutically acceptable salt of butorphanol is preferably a tartaric acid addition salt (butorphanol tartrate) represented by the following structural formula (1).

[Chem. 1]

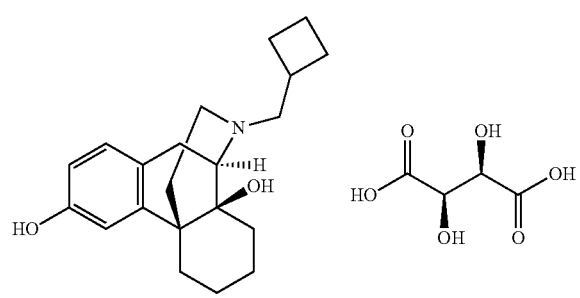

(1)

In the present invention, the content of butorphanol and/or a pharmaceutically acceptable salt thereof contained in the adhesive layer (the content of butorphanol, the content of a pharmaceutically acceptable salt of butorphanol, or their total content in the case where both of them are contained, hereinafter the same) is preferably 3 to 9% by mass, more preferably 3 to 6% by mass, and further preferably 3 to 5% by mass relative to the total mass of the adhesive layer in terms of a tartaric acid addition salt of butorphanol. When the content of butorphanol and/or a pharmaceutically acceptable salt thereof is less than the lower limit, the skin permeation rate and the skin permeation amount of butorphanol tend to decrease. On the other hand, when the upper limit is exceeded, there is a tendency that crystals of butorphanol precipitate, the adhesive force of the adhesive layer is lowered, and the performance of the patch such as the uniformity of the content is impaired.

In other words, when the content of butorphanol and/or a pharmaceutically acceptable salt thereof as a drug is in a range of 3 to 9% by mass (more preferably 3 to 6% by mass and further preferably 3 to 5% by mass), there is a tendency that it is possible to sufficiently shorten the lag time and the maximum skin permeation rate reach time (Tmax), to further increase the skin permeation rate and the skin permeation amount of the drug, and to dissolve an appropriate amount of drug crystal in an adhesive base.

It is necessary for the adhesive layer according to the present invention to contain a silicone-based adhesive base as an adhesive base. When the adhesive layer contains the silicone-based adhesive base, it is possible to sufficiently shorten the lag time and the maximum skin permeation rate reach time (Tmax) and, while keeping the utilization rate of the drug sufficiently high, further to sufficiently increase the skin permeation rate and the skin permeation amount of the drug even when the concentration and the absolute amount of the drug in the adhesive layer have been reduced. In addition, when the silicone-based adhesive base is contained as the adhesive base, it is possible to more improve the skin adhering properties of the adhesive layer.

In the present invention, the silicone-based adhesive base indicates a polymer (polysiloxane) which contains a siloxane unit represented by the following structural formula (2) and which has a siloxane bond (—Si—O—) as a main chain.

[Chem. 2]

(2)

In the siloxane unit represented by the formula (2), n represents a number of 2 or more. In addition, $R^1$ and $R^2$ each independently represent a group bonded to the Si atom. Preferably, $R^1$ and $R^2$ are, although not particularly limited, each independently a hydrogen atom, a hydroxyl group, an alkyl group, an alkenyl group, an aryl group, or an alkoxy group. In addition, the polymer may be any of linear, branched, and cyclic polymers, or may be a composite of these. Preferably, the end of the polymer is, although not particularly limited, each independently a hydrogen atom, a hydroxyl group, an alkyl group, an alkenyl group, an aryl group, an alkoxy group, a trimethylsilyl group, or a trimethylsilyloxy group.

Examples of the silicone-based adhesive base according to the present invention include, in the ASTM standards (ASTM D 1418), silicone rubbers represented by MQ (polydimethylsiloxane, $R^1$ and $R^2$ in the formula (2) are methyl groups), VMQ (polymethylvinylsiloxane), PMQ (polymethylphenylsiloxane), and PVMQ (polyphenylvinyl-methylsiloxane) as well as mixtures of at least one of these and silicone resins other than silicone rubbers such as polyditrimethylsilyl siloxane, and these may be used singly or two or more kinds thereof may be used in combination. Note that the silicone resins other than silicone rubbers mixed are preferably 0.5 to 20% by mass relative to the total mass of the silicone-based adhesive base.

In addition, commercial products may be used as these silicone-based adhesive bases, and usable examples thereof include silicone adhesives provided by Dow Corning under the following product code: BIO-PSA7-410X, BIO-PSA7-420X, BIO-PSA7-430X, BIO-PSA7-440X, BIO-PSA7-450X, BIO-PSA7-460X (the X's are each independently 1 or 2), BIO-PSA AC7-4201, BIO-PSA AC7-4301, BIO-PSA AC7-4302, MD7-4502, MD7-4602, 7-9700, MG7-9800, MG7-9850, a hot melt silicone adhesive BIO-PSA 7-4560, and the like. These may be used singly or two or more kinds thereof may be used in combination.

Moreover, for the purpose of enhancing the cohesiveness, the silicone-based adhesive base according to the present invention may be, in the case of having methyl groups, one in which a peroxide is blended to dehydrogenate the hydrogen atoms of the methyl group, followed by crosslinking of those methyl groups; in the case of having vinyl groups, one in which a crosslinking agent composed of an SiH group-containing siloxane compound is bonded to crosslink those vinyl groups; in the case of having hydroxyl groups (that is, in the case of having silanol groups), one in which those silanol groups are crosslinked by dehydration condensation, and the like.

In the present invention, the content of the silicone-based adhesive base contained in the adhesive layer is preferably 50 to 97% by mass, more preferably 60 to 90% by mass, and further preferably 65 to 85% by mass relative to the total mass of the adhesive layer. When the content of the silicone-based adhesive base is less than the lower limit, there is a tendency that the utilization rate of butorphanol is lowered and the adhesive force of the adhesive layer is lowered. On the other hand, when the upper limit is exceeded, the content of e.g. butorphanol and/or a pharmaceutically acceptable salt thereof and the absorption enhancer described below in the adhesive layer is relatively reduced, which tends to reduce the skin permeation amount of butorphanol.

The adhesive layer according to the present invention preferably further includes an absorption enhancer (transdermal absorption enhancer). The absorption enhancer is at least one selected from the group consisting of aliphatic alcohols, fatty acid esters, fatty acid amides, and aliphatic alcohol ethers. Among these, at least one selected from the group consisting of aliphatic alcohols and fatty acid esters is preferable from the viewpoint that the maximum skin permeation rate (Jmax) of butorphanol and/or a pharmaceutically acceptable salt thereof is particularly large.

(Aliphatic Alcohol)

The aliphatic alcohol according to the present invention is preferably an aliphatic alcohol having 6 to 20 carbon atoms. The skin irritation tends to be strong when the number of carbon atoms of the aliphatic alcohol is less than the lower limit, and on the other hand, waxy lumps may be formed in the preparation when the upper limit is exceeded. Examples of the aliphatic alcohol having 6 to 20 carbon atoms include lauryl alcohol, myristyl alcohol, cetyl alcohol, stearyl alcohol, isostearyl alcohol, oleyl alcohol, linolenyl alcohol, octyldodecanol, and mixtures thereof. Among these, at least one selected from the group consisting of isostearyl alcohol, oleyl alcohol, and octyldodecanol from the viewpoint that the skin permeability of butorphanol and/or a pharmaceutically acceptable salt thereof is more favorable.

(Fatty Acid Ester)

The fatty acid ester according to the present invention is preferably at least one selected from the group consisting of alkyl esters of fatty acids (fatty acid alkyl esters) having 6 to 20 carbon atoms, esters of fatty acids having 6 to 20 carbon atoms with glycerin or polyglycerin (glycerin fatty acid esters), esters of fatty acids having 6 to 20 carbon atoms with polyoxyalkylenes (polyoxyalkylene fatty acid esters), and esters of fatty acids having 6 to 20 carbon atoms with saccharides (fatty acid esters of saccharides).

In the present invention, the fatty acid alkyl ester is an ester compound of a fatty acid having 6 to 20 carbon atoms with an alkyl alcohol (preferably a lower alkyl alcohol). Examples of such a fatty acid alkyl ester include isopropyl myristate, oleyl oleate, isopropyl palmitate, triethyl citrate, ethyl linoleate, hexyl laurate, cetyl myristate, octyldodecyl myristate, decyl oleate, octyldodecyl oleate, octyldodecyl neodecanoate, cetyl ethylhexanoate, cetyl palmitate, stearyl stearate, and mixtures thereof. Among these, at least one selected from the group consisting of isopropyl myristate and isopropyl palmitate is preferable from the viewpoint that the skin permeability of butorphanol and/or a pharmaceutically acceptable salt thereof is more favorable.

In the present invention, examples of the glycerin fatty acid esters include glycerin monolaurate (monolaurin), polyglycerin monolaurate, glycerin monostearate (monostearin), polyglycerin monostearate, glycerin monooleate (monoolein), polyglycerin monooleate, glycerin trimyristate, caprylic/capric triglyceride, glycerin triisostearate, and glycerin trioctanoate. The degree of polymerization of the polyglycerin is preferably 50 or less. Among these, at least one selected from the group consisting of glycerin monolaurate, polyglycerin monolaurate, glycerin monostearate, polyglycerin monostearate, glycerin monooleate, and polyglycerin monooleate is preferable as the glycerin fatty acid ester.

In addition, the glycerin fatty acid ester may be one further added with a polyoxyethylene (POE) group to the OH group of glycerin. The degree of polymerization of the oxyethylene in the polyoxyethylene group is preferably 50 or less.

In the present invention, the polyoxyalkylene fatty acid ester is a compound in which the carboxy group moiety of a fatty acid having 6 to 20 carbon atoms is ester-bonded with a polyoxyalkylene such as ethylene glycol, polyethylene glycol, propylene glycol, polypropylene glycol, or a copolymer compound of oxyethylene and oxypropylene. Examples of such a polyoxyalkylene fatty acid ester include ethylene glycol monolaurate, polyoxyethylene monolaurate (hereinafter, polyoxyethylene is referred to as "POE" and oxyethylene as "OE" in some cases), propylene glycol monolaurate (PGML), polyoxypropylene monolaurate (hereinafter, polyoxypropylene is referred to as "POP" and oxypropylene as "OP" in some cases), ethylene glycol monopalmitate, POE monopalmitate, propylene glycol monopalmitate, POP monopalmitate, ethylene glycol monostearate, POE monostearate, propylene glycol monostearate, POP monostearate, ethylene glycol monooleate, POE monooleate, propylene glycol monooleate, POP monooleate, propylene glycol dioleate, and polyethylene glycol distearate. In copolymers of POE with POP and OE with OP, the degree of polymerization is preferably each independently 50 or less. Among these, propylene glycol monolaurate is particularly preferable as the polyoxyalkylene fatty acid ester from the viewpoint that the maximum skin permeation rate (Jmax) of butorphanol and/or a pharmaceutically acceptable salt thereof is particularly large.

In the present invention, the fatty acid ester of a saccharide is a compound in which the carboxy group moiety of a fatty acid having 6 to 20 carbon atoms is ester-bonded with a saccharide. Examples of the saccharide include tetroses (erythrose and threose), pentoses (xylose and arabinose), hexoses (glucose and galactose), sugar alcohols (xylitol and sorbitol), and disaccharides (sucrose, lactose, and maltose). Examples of the fatty acid esters of such saccharides include sorbitan monolaurate (Span 20), sorbitan monopalmitate (Span 40), sorbitan monostearate (Span 60), sorbitan tristearate (Span 65), sorbitan monooleate (Span 80), sorbitan trioleate, and sorbitan sesquioleate (Span 83).

In addition, the fatty acid ester of a saccharide may be one further added with a polyoxyethylene (POE) group to the OH group in the sugar residue. The degree of polymerization of the oxyethylene in the polyoxyethylene group is preferably 50 or less. Examples of such a compound include Polysorbate 20 (Tween 20), Polysorbate 40 (Tween 40), Polysorbate 60 (Tween 60), Polysorbate 65 (Tween 65), and Polysorbate 80 (Tween 80).

(Fatty Acid Amide)

The fatty acid amide according to the present invention is an amide of a fatty acid having 6 to 20 carbon atoms, and examples thereof include lauric acid diethanolamide, oleic acid diethanolamide, stearic acid diethanolamide, ethylene bis-stearamide, stearic acid monoamide, oleic acid monoamide, ethylene bis-oleamide, erucic acid monoamide, and mixtures thereof.

(Aliphatic Alcohol Ether)

In the present invention, the aliphatic alcohol ether is a compound in which the OH group moiety of an aliphatic alcohol having 6 to 20 carbon atoms is ether-bonded with a polyoxyalkylene such as ethylene glycol, polyethylene glycol, propylene glycol, polypropylene glycol, a copolymer compound of oxyethylene and oxypropylene, glycerin, or polyglycerin. Examples of such an aliphatic alcohol ether include POE oleyl ethers, POE lauryl ethers, POE cetyl ethers, POE stearyl ethers, POE octyldodecyl ethers, POE palmityl ethers, and mixtures thereof.

Other examples of the absorption enhancer which may be contained in the adhesive layer according to the present invention include POE hardened castor oils, lecithins, phospholipids, soybean oil derivatives, and triacetin.

In addition, the adhesive layer according to the present invention is preferably a surfactant compound in which the absorption enhancer functions as a surfactant. Examples of such a surfactant compound is, among the above, at least one selected from the group consisting of propylene glycol monolaurate, sorbitan monooleate, glycerin monolaurate, glycerin monooleate, Polysorbate 20, Polysorbate 40, Polysorbate 60, and Polysorbate 80. In addition, the surfactant compound is preferably nonionic.

In the present invention, the content of the absorption enhancer contained in the adhesive layer is preferably such an amount that the mass ratio of butorphanol and/or a pharmaceutically acceptable salt thereof to the absorption enhancer (mass of butorphanol and/or a pharmaceutically acceptable salt thereof in terms of a tartaric acid addition salt:mass of the absorption enhancer) is 2:1 to 1:4 and more preferably 2:1 to 1:3. When the content of the absorption enhancer is in the above range, there is a tendency that it is possible to more shorten the lag time and the maximum skin permeation rate reach time (Tmax), to further increase the skin permeation rate and the skin permeation amount of the drug, and moreover to increase the utilization rate even when the concentration and the absolute amount of butorphanol and/or a pharmaceutically acceptable salt thereof are comparatively small. On the other hand, when the content of the absorption enhancer is less than the lower limit, the maximum skin permeation rate reach time (Tmax) and the lag time of butorphanol tend to be long, and when the upper limit is exceeded, there is a tendency that crystals originating from butorphanol precipitate with time and the adhesive force is lowered due to a qualitative change in the adhesive layer.

In addition, in the present invention, the content of the absorption enhancer relative to the total mass of the adhesive layer is preferably 1.5 to 25% by mass, more preferably 2 to 25% by mass, and further preferably 3 to 20% by mass. When the content of the absorption enhancer is less than the lower limit, the maximum skin permeation rate reach time (Tmax) and the lag time of butorphanol tend to be long. On the other hand, when the upper limit is exceeded, there is a tendency that crystals originating from butorphanol precipitate with time and the adhesive force of the adhesive layer is lowered.

The adhesive layer according to the present invention may further contain an additive such as an adsorbent, a desalting agent, a tackifier, a plasticizer, a stabilizer, a solubilizer for the drug, a filler, or a preservative as long as the effects of the present invention are not impaired.

(Adsorbent)

Examples of the adsorbent include inorganic and/or organic substances having hygroscopicity, and more specific examples thereof include minerals such as talc, kaolin, and bentonite; silicon compounds such as fumed silica (such as Aerosil (registered trademark)) and hydrated silica; metal compounds such as zinc oxide and dried aluminum hydroxide gel; weak acids such as lactic acid and acetic acid; saccharides such as dextrin; and high molecular polymers such as polyvinylpyrrolidones, aminoalkyl methacrylate copolymers, crospovidone, carboxyvinyl polymers, and butyl methacrylate methyl methacrylate copolymers. These may be used singly or two or more kinds thereof may be used in combination. Among these, the adhesive layer according to the present invention preferably further contains polyvinylpyrrolidone (PVP) from the viewpoint that it is possible to suppress precipitation of crystals originating from butorphanol.

When the adsorbent (preferably polyvinylpyrrolidone) is further contained in the adhesive layer, the content thereof is preferably 0.05 to 2 mg/cm$^2$ as the content per unit area of the adhesive layer and preferably 1 to 20% by mass as the content relative to the total mass of the adhesive layer. Moreover, the mass ratio of butorphanol and/or a pharmaceutically acceptable salt thereof to the adsorbent (preferably polyvinylpyrrolidone) (mass of butorphanol and/or a pharmaceutically acceptable salt thereof in terms of a tartaric acid addition salt:mass of the adsorbent) is preferably 3:1 to 1:4. When the content of the polyvinylpyrrolidone is less than the lower limit, crystals originating from butorphanol tend to easily precipitate. On the other hand, when the upper limit is exceeded, there is a tendency that the skin permeability of butorphanol and/or a pharmaceutically acceptable salt thereof is lowered and the adhesive force of the adhesive layer is lowered.

(Desalting Agent)

The desalting agent is blended mainly for the purpose of converting all or a part of the basic drug into a free form. Although not particularly limited, such a desalting agent is preferably a basic substance and more preferably a metal ion-containing desalting agent or a basic nitrogen atom-containing desalting agent in the case of blending an acid addition salt of butorphanol as the drug to obtain a preparation containing a butorphanol free form. Examples of the metal ion-containing desalting agent include sodium acetate (including anhydrous sodium acetate), sodium hydroxide, potassium hydroxide, magnesium hydroxide, sodium hydrogen carbonate, and potassium hydrogen carbonate. These may be used singly or two or more kinds thereof may be used in combination. Among these, sodium acetate and sodium hydroxide are particularly preferable as the desalting agent. Note that the adhesive layer according to the present invention may further contain a compound derived from the basic drug and the desalting agent (for example, sodium tartrate in the case of combining butorphanol tartrate with sodium acetate). When such a desalting agent and a compound derived from the basic drug and the desalting agent are further contained in the adhesive layer, the content thereof is preferably 0.5 to 5 equivalents and more preferably 0.5 to 4 in an acid-base equivalent amount in terms of the desalting agent relative to acid-base equivalent amount 1 in terms of a tartaric acid addition salt of butorphanol from the viewpoint of suppressing the decomposition of the drug.

(Tackifier)

The tackifier is blended mainly for the purpose of enhancing the adhesion of the adhesive base. Examples of such a tackifier include rosin-based resins, terpene-based resins, petroleum-based resins, phenol-based resins, and xylene-based resins. These may be used singly or two or more kinds thereof may be used in combination. When such a tackifier is further contained in the adhesive layer, the content thereof is preferably 0.5 to 20% by mass and more preferably 3 to 15% by mass relative to the total mass of the adhesive layer from the viewpoint of improving the adhesive force of the adhesive layer and/or reducing the local irritation at the time of peeling off.

(Plasticizer)

The plasticizer is blended mainly for the purpose of adjusting the adhesive properties of the adhesive layer, the flow characteristics in the manufacture of the adhesive layer, the transdermal absorption characteristics of the drug, and the like. Examples of such a plasticizer include silicone oils; petroleum-based oils such as paraffinic process oils, naphthenic process oils, and aromatic process oils; squalane and squalene; vegetable-based oils such as olive oil, camellia oil, castor oil, tall oil, and peanut oil, dibasic esters such as dibutyl phthalate and dioctyl phthalate; liquid rubbers such as polybutene and liquid isoprene rubber; and diethylene glycol, polyethylene glycol, propylene glycol, and dipropylene glycol. These may be used singly or two or more kinds thereof may be used in combination. Among these, silicone oils, liquid paraffin, and liquid polybutene are preferable as the plasticizer.

(Solubilizer)

The solubilizer is blended mainly for the purpose of promoting dissolution of the drug. Examples of such a solubilizer include organic acids such as acetic acid, aliphatic alcohols, and surfactants. These may be used singly or two or more kinds thereof may be used in combination. Among these, organic acids and aliphatic alcohols are preferable as the solubilizer.

(Filler)

The filler is blended mainly for the purpose of adjusting the adhesive force of the adhesive layer. Examples of such a filler include aluminum hydroxide, calcium carbonate, and magnesium carbonate; silicates such as aluminum silicate and magnesium silicate; and silicic acid, barium sulfate, calcium sulfate, calcium zincate, zinc oxide, and titanium oxide. These may be used singly or two or more kinds thereof may be used in combination.

It is necessary for the adhesive layer according to the present invention to have a mass per unit area (area of the application surface) of 30 to 90 g/m$^2$. When the mass per unit area is less than the lower limit, the skin permeation rate and skin permeation amount of the drug is significantly lowered and the adhesive force of the adhesive layer is lowered. In addition, there is a tendency that it becomes difficult to control the thickness of the adhesive layer during manufacture or the backing layer directly comes into contact with the skin at the time of application to cause physical stimulation. On the other hand, when the mass per unit area exceeds the upper limit, the lag time and the maximum skin permeation rate reach time (Tmax) become longer and the utilization rate of the drug is lowered. The mass per unit area of the adhesive layer is more preferably 40 to 90 g/m$^2$ and particularly preferably 40 to 80 g/m$^2$ from the viewpoint that there is a tendency that it is possible to more shorten the lag time and the maximum skin permeation rate reach time (Tmax), to keep the skin permeation rate and skin permeation amount of the drug in a favorable range, and to increase the utilization rate.

In addition, the area of the application surface of the adhesive layer according to the present invention can be appropriately adjusted depending on the therapeutic purpose and the target for application, and is usually in a range of 0.5 to 150 cm$^2$.

The patch of the present invention makes it possible to sufficiently shorten the lag time and the maximum skin permeation rate reach time (Tmax). The lag time is preferably 5 hours or less in the case where the mass per unit area of the application surface of butorphanol and/or a pharmaceutically acceptable salt thereof contained the adhesive layer is 0.36 mg/cm$^2$ or less in terms of a tartaric acid addition salt of butorphanol (for example, in the case where the content of butorphanol and/or a pharmaceutically acceptable salt thereof contained in the adhesive layer is 4%, by mass in terms of a tartaric acid addition salt of butorphanol and the mass per unit area of the adhesive layer is 90 g/m$^2$ or less). In addition, the maximum skin permeation rate reach time (Tmax) is preferably less than 14 hours and more preferably 10 hours or less in the case where the mass per unit area of the application surface of butorphanol and/or a pharmaceutically acceptable salt thereof contained in the adhesive layer is 0.36 mg/cm$^2$ or less in terms of a tartaric acid addition salt of butorphanol.

In the present invention, the lag time and the maximum skin permeation rate reach time (Tmax) are specifically obtained by the following method. Note that although the lag time can also be obtained by skin thickness and drug diffusion coefficient in skin as described above, the lag time is obtained by the following method in the present invention. First, a patch is applied to the epidermis side of the trunk of a hairless mouse from which fat has been removed, and the dermis side is set in contact with a receptor solution (preferably PBS, 32° C.). While feeding the receptor solution at a flow rate of about 2.5 ml/hr, the receptor solution is collected at predetermined time intervals. The concentration of butorphanol in the collected receptor solution (in terms of a tartaric acid addition salt) is measured by e.g. high performance liquid chromatography to calculate the accumulated skin permeation amount of butorphanol per unit area of the application surface at each time interval (in terms of a tartaric acid addition salt, unit: µg/cm$^2$) and the skin permeation amount of butorphanol per unit area of the application surface per 1 hour, that is, the skin permeation rate (in terms of a tartaric acid addition salt, unit: µg/cm$^2$/hr). Next, consider an accumulated skin permeation amount-time curve obtained by setting the x axis as the time from the start of application (hours [hr]) and the y axis as the accumulated skin permeation amount. An approximate straight line is drawn at the point where the variation of y reached the steady state (the point where the skin permeation rate has shifted to the steady state). The value of the x intercept where that straight line crosses the x axis can be obtained as the lag time (delay time for the skin permeation rate to reach the steady state, unit: hr). In addition, from the rate-time curve obtained by setting the x axis as the time from the start of application (hours [hr]) and the y axis as the skin permeation rate, the maximum skin permeation rate reach time (Tmax, unit: hr) can be obtained as the value of x when y reaches the maximum value.

The butorphanol-containing patch of the present invention is not particularly limited, and can be manufactured by appropriately employing a known patch manufacturing method. For example, first, butorphanol and/or a pharmaceutically acceptable salt thereof, the silicone-based adhesive base, and, if necessary, the absorption enhancer, a solvent, and the additive are kneaded in accordance with a conventional method to obtain a uniform adhesive layer composition. Examples of the solvent include anhydrous ethanol and toluene. Next, this adhesive layer composition is applied on the surface (usually on one surface) of the backing layer to the mass per unit area described above, followed by heating if necessary. The solvent is removed by drying to form an adhesive layer, followed by, if necessary, further cutting into a desired shape to obtain the patch of the present invention.

In addition, the method for manufacturing the butorphanol-containing patch of the present invention may further include the step of bonding the release liner on a surface of the adhesive layer opposite to the backing layer, in which the patch of the present invention is obtained by first forming an adhesive layer by applying the adhesive layer composition on one surface of the release liner to the mass per unit area described above, then bonding the backing layer on a surface of the adhesive layer opposite to the release liner, and, if necessary, cutting the resultant into a predetermined shape. Moreover, if necessary, the obtained patch may be enclosed in a storage packaging container (for example, an aluminum-laminated bag) to form a package.

EXAMPLES

Hereinafter, the present invention is described more specifically based on Examples and Comparative Examples, but the present invention is not limited to the following Examples. In Examples and Comparative Examples, skin permeation tests were carried out by the following methods.

<Skin Permeation Test ((In Vitro) Hairless Mouse Skin Permeation Test)>

First, the skin of the trunk of a hairless mouse was peeled off, and the fat was removed from the skin. Then, a patch which had been subjected to cutting into a size of 2 or 2.5 cm$^2$ and removal of the release liner was applied to the epidermis side of the skin. This was set in a Franz permeation test cell of a flow-through type such that the dermis side came into contact with a receptor solution, and the cell was filled with the receptor solution (PBS). Subsequently, the receptor solution was fed at a flow rate of approximately 2.5 mL/hr while circulating a circulation water, which had been warmed such that the receptor solution was kept at a temperature of 32° C., around the outer periphery. Then, the receptor solution was collected or every 4 hours for 24 hours. The concentration of butorphanol in the collected receptor solution (in terms of a tartaric acid addition salt) was measured by high performance liquid chromatography to calculate the accumulated skin permeation amount of butorphanol per unit area of the application surface at each time interval (in terms of a tartaric acid addition salt, unit: $\mu g/cm^2$) and the skin permeation amount of butorphanol per unit area of the application surface per 1 hour (in terms of a tartaric acid addition salt, unit: $\mu g/cm^2/hr$).

Next, the lag time (hr) was obtained by the above method from the accumulated skin permeation amount-time curve obtained by setting the x axis as the time from the start of application (hr) and the y axis as the accumulated skin permeation amount. In addition, from the rate-time curve obtained by setting the x axis as the time from the start of application (hr) and the y axis as the skin permeation rate, the maximum value of y was determined as the maximum skin permeation rate (Jmax) and the value of x when y reached the maximum value was determined as the maximum skin permeation rate reach time (Tmax). Moreover, the accumulated skin permeation amount 24 hours after the start of application was defined as the 24-hr accumulated skin permeation amount (A, unit: $\mu g/cm^2$), which was used together with the content (B) per unit area of butorphanol in the adhesive layer of the patch before the start of application in terms of a tartaric acid addition salt to define the value obtained by the following formula: A/B×100 as the 24-hr drug utilization rate (utilization rate of the drug, %).

Example 1

First, 4.0 parts by mass of butorphanol tartrate, 1.4 parts by mass of sodium acetate as the desalting agent, 5.0 parts by mass of oleyl alcohol, 9.0 parts by mass of polyvinylpyrrolidone (PVP), 10.0 parts by mass of tackifier (terpene-based resin), 1.4 parts by mass of plasticizer (silicone oil), and 69.2 parts by mass of silicone-based adhesive base 1 (silicone adhesive, product code: BIO-PSA7-4201, manufactured by Dow Corning) were measured out, and an appropriate amount of a solvent (anhydrous ethanol and toluene) was added, followed by mixing to obtain an adhesive layer composition.

Table 1 below shows the composition of the adhesive layer composition (excluding the solvent). Next, the obtained adhesive layer composition was applied on a release liner (polyethylene terephthalate film subjected to release treatment), and the solvent was removed by drying and formation was carried out so that the mass per unit area of the adhesive layer was 40 g/m². A backing layer (polyethylene terephthalate film) was stacked on the surface of the obtained adhesive layer opposite to the release liner to obtain a patch stacked in the order of backing layer/adhesive layer/release liner.

TABLE 1

|  | Parts by Mass |
|---|---|
| Butorphanol Tartrate | 4.0 |
| Sodium Acetate | 1.4 |
| Oleyl Alcohol | 5.0 |
| Polyvinylpyrrolidone | 9.0 |
| Tackifier | 10.0 |
| Plasticizer | 1.4 |
| Silicone-Based Adhesive Base 1 | 69.2 |
| Total | 100.0 |

Examples 2 to 4 and Comparative Examples 1 to 3

The patches were obtained in the same manner as that of Example 1 except that the masses per unit area of the adhesive layers were the masses shown in Table 2 below.

Comparative Example 4

First, 9.0 parts by mass of butorphanol tartrate, 3.1 parts by mass of sodium acetate as the desalting agent, 7.0 parts by mass of oleyl alcohol, 9.0 parts by mass of polyvinylpyrrolidone (PVP), and 71.9 parts by mass of rubber-based adhesive base 1 were measured out, and an appropriate amount of a solvent (anhydrous ethanol and toluene) was added, followed by mixing to obtain an adhesive layer composition. The rubber-based adhesive base 1 used was a mixture of 50 parts by mass of styrene-isoprene-styrene block copolymer (SIS), 50 parts by mass of polyisobutylene (PIE), 115.4 parts by mass of tackifier (terpene-based resin), and 61.5 parts by mass of liquid paraffin.

Next, the obtained adhesive layer composition was applied on a release liner (polyethylene terephthalate film subjected to release treatment), and the solvent was removed by drying and formation was carried out so that the mass per unit area of the adhesive layer was 81 g/m². A backing layer (polyethylene terephthalate film) was stacked on the surface of the obtained adhesive layer opposite to the release liner to obtain a patch stacked in the order of backing layer/adhesive layer/release liner.

A skin permeation test was carried out on each of the patches obtained in Examples 1 to 4 and Comparative Examples 1 to 4. Table 2 shows the results obtained in Examples 1 to 4 and Comparative Examples 1 to 3 together with the masses per unit area of the adhesive layers. In addition, the 24-hr drug utilization rate in Comparative Example 4 was 58%.

TABLE 2

|  | Comparative Example 1 | Example 1 | Example 2 | Example 3 | Example 4 | Comparative Example 2 | Comparative Example 3 |
|---|---|---|---|---|---|---|---|
| Mass of Adhesive Layer [g/m²] | 25 | 40 | 52 | 63 | 81 | 94 | 114 |
| Maximum Skin Permeation Rate (Jmax) [μg/cm²/hr] | 8.6 | 10.1 | 12.0 | 14.2 | 13.4 | 11.7 | 13.5 |
| 24-hr Accumulated Skin Permeation Amount [μg/cm²] | 94 | 139 | 176 | 202 | 218 | 197 | 218 |
| Lag Time [hr] | 2.6 | 2.9 | 3.1 | 3.9 | 4.8 | 5.5 | 6.3 |
| Maximum Skin Permeation Rate Reach Time (Tmax) [hr] | 6 | 10 | 10 | 10 | 10 | 14 | 14 |
| 24-hr Drug Utilization Rate [%] | 94 | 87 | 88 | 84 | 68 | 55 | 47 |

Examples 5 to 7

The patches were obtained in the same manner as that of Example 1 except that the compositions of the adhesive layer compositions were the compositions shown in Table 3 below and the masses per unit area of the adhesive layers were 90 g/m². Specifically, the patches were obtained in the same manner as that of Example 1 except that polyvinylpyrrolidone was not used, oleyl alcohol was replaced with isostearyl alcohol (Example 5), octyldodecanol (Example 6), and propylene glycol monolaurate (Example 7), and the silicone-based adhesive base 1 was replaced with silicone-based adhesive 2 (silicone adhesive, product code: BIO-PSA7-4302, manufactured by Dow Corning) and that the tackifier was 11.1 parts by mass, the plasticizer was 1.6 parts by mass, and the silicone-based adhesive base 2 was 76.9 parts by mass.

A skin permeation test was carried out on each of the patches obtained in Examples 5 to 7. Table 3 shows the obtained results together with the compositions of the adhesive layer compositions (excluding the solvent) and the masses per unit area of the adhesive layers.

TABLE 3

|  | Example 5 | Example 6 | Example 7 |
| --- | --- | --- | --- |
| Butorphanol Tartrate | 4.0 | 4.0 | 4.0 |
| Sodium Acetate | 1.4 | 1.4 | 1.4 |
| Isostearyl Alcohol | 5.0 | — | — |
| Octyldodecanol | — | 5.0 | — |
| Propylene Glycol Monolaurate | — | — | 5.0 |
| Tackifier | 11.1 | 11.1 | 11.1 |
| Plasticizer | 1.6 | 1.6 | 1.6 |
| Silicone-Based Adhesive Base 2 | 76.9 | 76.9 | 76.9 |
| Total [Parts by Mass] | 100.0 | 100.0 | 100.0 |
| Mass of Adhesive Layer [g/m²] | 90 | 90 | 90 |
| Lag Time [hr] | 3.9 | 3.7 | 3.0 |
| Maximum Skin Permeation Rate Reach Time (Tmax) [hr] | 10 | 10 | 10 |

Example 8

The patch was obtained in the same manner as that of Example 1 except that the composition of the adhesive layer composition and the mass per unit area of the adhesive layer were the composition and the mass shown in Table 4 below. Specifically, the patch was obtained in the same manner as that of Example 1 except that the tackifier and the plasticizer were not used, the silicone-based adhesive base 1 was replaced with 80.6 parts by mass of silicone-based adhesive 3 (silicone adhesive, product code: BIO-PSA AC7-4201, manufactured by Dow Corning), and the mass per unit area of the adhesive layer was set to 44 g/m².

Example 9

The patch was obtained in the same manner as that of Example 8 except that the butorphanol tartrate and the sodium acetate were replaced with 2.7 parts by mass of butorphanol (free form) and the mass per unit area of the adhesive layer was set to 48 g/m².

A skin permeation test was carried out on each of the patches obtained in Examples 8 and 9. Table 4 shows the obtained results together with the compositions of the adhesive layer compositions (excluding the solvent) and the masses per unit area of the adhesive layers.

TABLE 4

|  | Example 8 | Example 9 |
| --- | --- | --- |
| Butorphanol Tartrate | 4.0 | — |
| Butorphanol (in Terms of Butorphanol Tartrate) | — | 2.7 (4.0) |
| Sodium Acetate | 1.4 | — |
| Oleyl Alcohol | 5.0 | 5.0 |
| Polyvinylpyrrolidone | 9.0 | 9.0 |
| Silicone-Based Adhesive Base 3 | 80.6 | 83.3 |
| Total [Parts by Mass] | 100.0 | 100.0 |
| Mass of Adhesive Layer [g/m²] | 44 | 48 |
| Lag Time [hr] | 2.9 | 3.6 |
| Maximum Skin Permeation Rate Reach Time (Tmax) [hr] | 10 | 10 |

Example 10 and Comparative Example 5

The patches were obtained in the same manner as that of Example 1 except that the compositions of the adhesive layers and the masses per unit area of the adhesive layer compositions were the compositions and the masses shown in Table 5 below. Specifically, the patch was obtained in the same manner as that of Example 1 except that the tackifier and the plasticizer were not used, the amount of butorphanol tartrate blended was 9.0 parts by mass, the amount of sodium acetate blended was 3.1 parts by mass, the silicone-based adhesive base 1 was replaced with 73.9 parts by mass of silicone-based adhesive 3, and the masses per unit area of the adhesive layers were set to 97 g/m² and 47 g/m².

Comparative Example 6

The patch was obtained in the same manner as that of Example 10 except that the silicone-based adhesive 3 was replaced with an acrylic adhesive base (2-ethylhexyl acrylate.2-ethylhexylmethacrylate.dodecyl methacrylate copolymer) and the mass per unit area of the adhesive layer was set to 45 g/m².

A skin permeation test was carried out on each of the patches obtained in Example 10 and Comparative Examples 5 and 6. Table 5 shows the obtained results together with the compositions of the adhesive layer compositions (excluding the solvent) and the masses per unit area of the adhesive layers.

TABLE 5

|  | Comparative Example 5 | Example 10 | Comparative Example 6 |
| --- | --- | --- | --- |
| Butorphanol Tartrate | 9.0 | 9.0 | 9.0 |
| Sodium Acetate | 3.1 | 3.1 | 3.1 |
| Oleyl Alcohol | 5.0 | 5.0 | 5.0 |
| Polyvinylpyrrolidone | 9.0 | 9.0 | 9.0 |
| Silicone-Based Adhesive Base 3 | 73.9 | 73.9 | — |
| Acrylic Adhesive Base | — | — | 73.9 |
| Total [Parts by Mass] | 100.0 | 100.0 | 100.0 |
| Mass of Adhesive Layer [g/m²] | 97 | 47 | 45 |
| Lag Time [hr] | 6.4 | 4.9 | 5.7 |
| Maximum Skin Permeation Rate Reach Time (Tmax) [hr] | 18 | 14 | 18 |

As is clear from the results shown in Tables 2 to 5, the patches of the present invention whose adhesive layers had masses per unit area of 90 g/m² or less were confirmed to have a particularly short lag time and maximum skin permeation rate reach time (Tmax) and a particularly high drug utilization rate. In addition, it was confirmed that the lag time and the maximum skin permeation rate reach time (Tmax) tended to become shorter and the drug utilization rate tended to be higher as the mass per unit area of the adhesive layer decreased. Moreover, comparison of the drug utilization rates of Example 4 and Comparative Example 4, whose adhesive layers had the same mass per unit area of 81 g/m², revealed that Comparative Example 4 had a 24-hr drug utilization rate of 58%, which was a sufficient utilization rate, whereas the patch of the present invention of Example 4 had an even higher drug utilization rate even though the content of the absorption enhancer (oleyl alcohol) was smaller than that of Comparative Example 4.

It was also confirmed that, even when the content (entire amount) of butorphanol was reduced due to a small mass per unit area of the adhesive layer, the patches of the present invention whose adhesive layers had a mass per unit area in a range of 30 to 90 g/m² had a sufficiently large maximum skin permeation rate (Jmax) as well as a 24-hr accumulated skin permeation amount kept sufficiently large. On the other hand, when the mass per unit area of the adhesive layer was less than 30 g/m², it was confirmed that maximum skin permeation rate (Jmax) and the 24-hr accumulated skin permeation amount were rapidly lowered.

INDUSTRIAL APPLICABILITY

As described above, the present invention makes it possible to provide a butorphanol-containing patch which has a sufficiently short lag time and maximum skin permeation rate reach time (Tmax) and which is sufficiently large in drug skin permeation amount as well as sufficiently high in utilization rate.

The invention claimed is:

1. A patch comprising:
   a backing layer; and
   an adhesive layer, wherein
   the adhesive layer contains at least one drug selected from the group consisting of butorphanol and pharmaceutically acceptable salts thereof and a silicone-based adhesive base,
   a content of the silicone-based adhesive base in the adhesive layer is 50 to 97% by mass relative to the total mass of the adhesive layer, and
   a mass per unit area of the adhesive layer is 40 to 80 g/m².

2. The patch according to claim 1, wherein
   the adhesive layer further contains at least one absorption enhancer selected from the group consisting of aliphatic alcohols and fatty acid esters.

3. The patch according to claim 2, wherein
   the absorption enhancer is at least one selected from the group consisting of isostearyl alcohol, oleyl alcohol, octyldodecanol, and propylene glycol monolaurate.

4. The patch according to claim 2, wherein
   a content of the absorption enhancer in the adhesive layer is 2:1 to 1:4 in a mass ratio of butorphanol and/or the pharmaceutically acceptable salt thereof (mass of butorphanol and/or the pharmaceutically acceptable salt thereof in terms of a tartaric acid addition salt of butorphanol:mass of the absorption enhancer).

5. The patch according to claim 2, wherein
   a content of the absorption enhancer in the adhesive layer is 1.5 to 25% by mass relative to a total mass of the adhesive layer.

6. The patch according to claim 1, wherein
   a content of butorphanol and/or the pharmaceutically acceptable salt thereof in the adhesive layer is 3 to 9% by mass relative to the total mass of the adhesive layer in terms of a tartaric acid addition salt of butorphanol.

7. The patch according to claim 1, wherein
   the adhesive layer further contains an adsorbent.

8. The patch according to claim 7, wherein
   a content of the adsorbent in the adhesive layer is 3:1 to 1:4 in a mass ratio of butorphanol and/or the pharmaceutically acceptable salt thereof (mass of butorphanol and/or the pharmaceutically acceptable salt thereof in terms of a tartaric acid addition salt of butorphanol: mass of the adsorbent).

9. The patch according to claim 7, wherein
   a content of the adsorbent in the adhesive layer is 1 to 20% by mass relative to the total mass of the adhesive layer.

* * * * *